United States Patent
Turner et al.

(10) Patent No.: US 12,280,273 B2
(45) Date of Patent: Apr. 22, 2025

(54) BASE DOSE CALCULATION

(71) Applicants: MIM SOFTWARE INC., Cleveland, OH (US); GT MEDICAL TECHNOLOGIES, INC., Tempe, AZ (US)

(72) Inventors: Adam Turner, Phoenix, AZ (US); Elliot M. Abbott, Boston, MA (US); David Brachman, Phoenix, AZ (US); Jonathan Piper, Orange, OH (US)

(*) Notice: Subject to any disclaimer, the term of this patent is extended or adjusted under 35 U.S.C. 154(b) by 228 days.

(21) Appl. No.: 17/985,704

(22) Filed: Nov. 11, 2022

(65) Prior Publication Data

US 2023/0144124 A1 May 11, 2023

Related U.S. Application Data (60) Provisional application No. 63/263,909, filed on Nov. 11, 2021.

(51) Int. Cl.
*A61N 5/10* (2006.01)
*G16H 20/40* (2018.01)

(52) U.S. Cl.
CPC ......... *A61N 5/1031* (2013.01); *A61N 5/1039* (2013.01); *G16H 20/40* (2018.01); *A61N 2005/1074* (2013.01)

(58) Field of Classification Search
CPC ........ A61N 5/10; A61N 5/1038; A61N 5/103; A61N 5/1031; A61N 2005/1032; A61N 2005/1034; A61N 2005/1035; A61N 5/1039; A61N 2005/1041; A61N 5/1048; A61N 5/1071; A61N 5/1064; A61N 5/1049; A61N 5/1067; A61B 6/5217; A61B 6/5288; A61B 6/5294
See application file for complete search history.

(56) References Cited

U.S. PATENT DOCUMENTS

2018/0369611 A1* 12/2018 Owens ................ A61N 5/1068
2021/0228907 A1   7/2021 Olcott et al.

OTHER PUBLICATIONS

Zhang, et al.; Generation of Composite Dose and Biological Effective Dose (BED) Over Multiple Treatment Modalities and Multistage Planning Using Deformable Image Registration; Medical Dosimetry; vol. 35, No. 2, Jun. 8, 2009; pp. 143-150; SP002808888; ISSN: 0958-3947, DOI: 10.1016/J. Meddos.2009.05.001; abstract chapters "introduction" and "Conclusions".
Tornero-Lopez Ana M. et al.; Radiobiological considerations in Combining does from external beam radiotherapy and brachytherapy for cervical cancer; Reports of Practical Oncology and Radiotherapy, GreatPoland Cancer Center/ Polish Society of Radiation Oncology, PL.; vol. 23, No. 6, Jul. 3, 2018; pp. 562-573; XP085553032; ISSN: 1507-1367, DOI: 10.1016/J. RPOR.2018.05.007; Abstract p. 564-565 and p. 568.

(Continued)

*Primary Examiner* — Don K Wong
(74) *Attorney, Agent, or Firm* — Tucker Ellis LLP (57) ABSTRACT

A base dose calculation tool for determining a base dose employed in treatment planning. Base therapy information is considered on a voxelized and temporal basis such that subsequent treatments may be planned. The base dose output is operable with existing treatment planning systems.

26 Claims, 9 Drawing Sheets

(56) References Cited

OTHER PUBLICATIONS

Notification of Transmittal of International Search Report and the Written Opinion of the International Searching Authority; PCT/US/2022/049727, mailed Apr. 17, 2023; 12 pages.

Journal of the ICRU; vol. 13, No. 1-2, 2013; Prescribing, Recording and Reporting Brachytherapy for Cancer of the Cervix; 260 pgs; ICRU 2016.

McVicar, Nevin, et al; Re-irradiation volumetric modulated arc therapy optimization based on cumulative biologically effective dose objects; Dept. of Medical Physics, BC Cancer Vancouver Cancer Centre, Vancouver, BC Canada; Dept of Radiation Oncology, BC Cancer—Vancouver Cancer Centre, Vancouver BC, Canada; Accepted Aug. 27, 2018. 5 pgs.

AAPM Report No. 166; The Use and QA of Biologically Related Models for Treatment Planning; Report of AAPM Task Group 166 of the Therapy Physics Committee; Mar. 2012; 70 pgs.; 212 pgs.

George Sgouros, et al.; ICRU Report No. 96, Dosimetry-Guided Radiopharmaceutical Therapy; 2021, vol. 21 (I) 1-212; copyright 2021, International Commission on Radiation Units & Measurements.

Yamada, et al.; American Brachytherapy Society consensus guidelines for high-dose-rate prostate brachytherapy; 2012; 13 pgs.

Zaider, et al.; The role of external beam in brachytherapy; Copyright 2007 Future Medicine Ltd. 10 pgs.

* cited by examiner

BASE DOSE CALCULATION

CROSS-REFERENCE TO RELATED APPLICATIONS

This application claims the benefit of and priority to U.S. Provisional Application No. 63/263,909, filed on Nov. 11, 2021. The entirety of the aforementioned application is incorporated herein by reference.

BACKGROUND OF THE INVENTION

Biological outcomes from a given dose of radiation vary based on specifics of particle type, three-dimensional dose distribution, dose rate, fractionation schedule, etc. Accordingly, physical dose alone does not provide an accurate method of comparing the expected biological effects between two or more courses of radiation therapy that vary by delivery modality, fractionation schedule, and particle energy and/or type. Examples of radiation treatment modalities for which direct physical dose comparison is inappropriate for biological effect considerations include conventional and hypofractionated external beam photon radiation therapy (EBRT), proton therapy, high dose rate (HDR) brachytherapy, and low dose rate (LDR) brachytherapy (BT). Further, simple summations of physical dose distributions from dissimilar treatment courses are not useful indicators of expected tumor control or normal tissue complication probabilities.

Biologically Effective Dose (BED) has been introduced to quantitatively model the biological effect of radiation therapy. The BED concept has evolved to account for several factors, including but not limited to dose rate and time between fractionated deliveries, to account for repair of sub-lethal damage and cellular repopulation during treatment. BED distributions from different forms of radiation therapy may be directly compared or summed together to appropriately evaluate an expected biological outcome from combined use of the radiation therapies.

BRIEF SUMMARY OF THE INVENTION

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of the summary is to present some concepts related to some exemplary non-limiting embodiments in a simplified form as a prelude to the more detailed description of the various embodiments that follow.

In various, non-limiting embodiments, a system and associated methods are provided for determining a base dose input to a treatment planning system (TPS). Prior therapy information related to prior radiation therapy performed on a patient is acquired. Further, plan therapy information related to an additional radiation therapy to be performed on the patient is obtained. A base dose is determined based on the prior therapy information and the future plan therapy information. The base dose is determined in accordance with a base dose relationship derived from a biological effective dose (BED) model associated with the plan therapy. The base dose is exported to a TPS for planning the future radiation therapy.

These and other embodiments are described in more detail below.

BRIEF DESCRIPTION OF THE DRAWING

Various non-limiting embodiments are further described with reference to the accompanying drawings in which.

DETAILED DESCRIPTION OF THE INVENTION

As discussed in the background, biologically effective dose (BED), unlike physical dose, can be utilized to evaluate and/or compare biological outcomes from various radiation therapies, and/or the combined use of various radiation therapies. Conversion of physical dose to BED may be based on a linear-quadratic (LQ) model that describes the probability of cells surviving after receiving varying amounts of radiation dose from varying particle types delivered at varying dose rates and/or fractionation schedules. The LQ model results from fitting a surviving fraction of irradiated cells as a function of physical dose through a second-order polynomial with coefficients $\alpha$ and $\beta$. Specifically, the LQ model indicates the surviving fraction of cells (S) irradiated with a dose (D) over a time period (T) as generally indicated by Equation 1.

$$S = e^{-E} \qquad \text{Equation 1}$$

In Equation 1, E represents a biological effectiveness of radiation exposure to a population of cells that causes inactivation that accounts for cell population. E may be defined according to Equation 2.

$$E = \alpha D + \beta G D^2 - \frac{\ln(2)}{T_P}(T - T_k) \qquad \text{Equation 2}$$

In Equation 2, $\alpha$ and $\beta$ are coefficients that account for tissue radiosensitivity, G accounts for dose rate and repair of sublethal damage (e.g. a dose protraction factor), $T_P$ is a tumor doubling time, and $T_K$ represents a kick-off period after the onset of radiation therapy prior to initiation of cell repopulation. The $\alpha$ and $\beta$ values are tissue-specific and express the radiosensitivity (e.g. sensitivity to fractionation). In exemplary applications, the LQ model provides an accurate description of fractionation effects at doses between 1 and 10 Gy per fraction.

BED may be related to Equation 1 and Equation 2, for example, according to Equation 3.

$$BED = \frac{E}{\alpha} = D + \frac{GD^2}{\frac{\alpha}{\beta}} - \frac{\ln(2)}{\alpha T_P}(T - T_K) \qquad \text{Equation 3}$$

Bed for Fractionated External Beam Radiation Therapy

A total dose ($D_{EBRT}$) from external beam radiation therapy (EBRT) may be delivered in a prescribed number of fractions ($n_{EBRT}$) of equal dose with a sublethal damage repair factor represented as $G=1/n_{EBRT}$. For EBRT, the effect of tumor cell repopulation may be ignored since a tumor "kick-off" period, $T_K$, is greater than a total treatment time, T. Substitution of these values into Equation 3 results in the widely used BED model for EBRT:

$$BED_{EBRT} = D_{EBRT}\left(1 + \frac{D_{EBRT}/n_{EBRT}}{\alpha/\beta}\right) \qquad \text{Equation 4}$$

Derivation of Method for Bed Informed Ebrt Planning Using Base Plan

This method assumes both an a priori known desired reference BED distribution ($BED_{ref}$) and the previously delivered BED distribution(s) ($BED_{prior}$). $BED_{ref}$ values can be calculated by converting accepted physical dose constraints (such as tumor prescription values and organ at risk tolerances) corresponding to a specified fractionation scheme using the appropriate BED model. For radiation target volumes (e.g. tumor), the $BED_{ref}$ distribution represents the desired minimum summation of the $BED_{prior}$ and $BED_{EBRT}$ at each point. For organs at risk (OAR), the $BED_{ref}$ represents a maximum BED volumetric statistic of the desired of the $BED_{prior}$ and $BED_{EBRT}$.

Assuming the prior physical dose distribution is known and a model exists to convert physical dose from the prior therapy modality to BED, it is mathematically straightforward to calculate the $BED_{prior}$ for each voxel. The remaining BED required to be delivered from future EBRT ($BED_{EBRT}$) is simply the difference between the $BED_{ref}$ and the $BED_{prior}$:

$$BED_{EBRT} = BED_{ref} - BED_{prior} \qquad \text{Equation 5}$$

However, EBRT TPS platforms optimize treatment plans using physical dose, not BED. So, it is necessary to convert the $BED_{EBRT}$ to physical dose ($D_{EBRT}$). This is done by solving Equation 4 for the EBRT dose ($D_{EBRT}$) in terms of $BED_{EBRT}$, the number of fractions ($n_{EBRT}$), and the alpha/beta ratio ($\alpha/\beta$). This results in a quadratic equation, where the positive solution is used:

$$D_{EBRT} = \frac{n_{EBRT}(\alpha/\beta)}{2}\left(-1 + \sqrt{1 + \frac{4BED_{EBRT}}{n_{EBRT}(\alpha/\beta)}}\right) \qquad \text{Equation 6}$$

Substitution for $BED_{EBRT}$ in terms of $BED_{ref}$ and $BED_{prior}$ (Equation 5), gives:

$$D_{EBRT} = \frac{n_{EBRT}(\alpha/\beta)}{2}\left(-1 + \sqrt{1 + \frac{4(BED_{ref} - BED_{prior})}{n_{EBRT}(\alpha/\beta)}}\right) \qquad \text{Equation 7}$$

Figure 1:
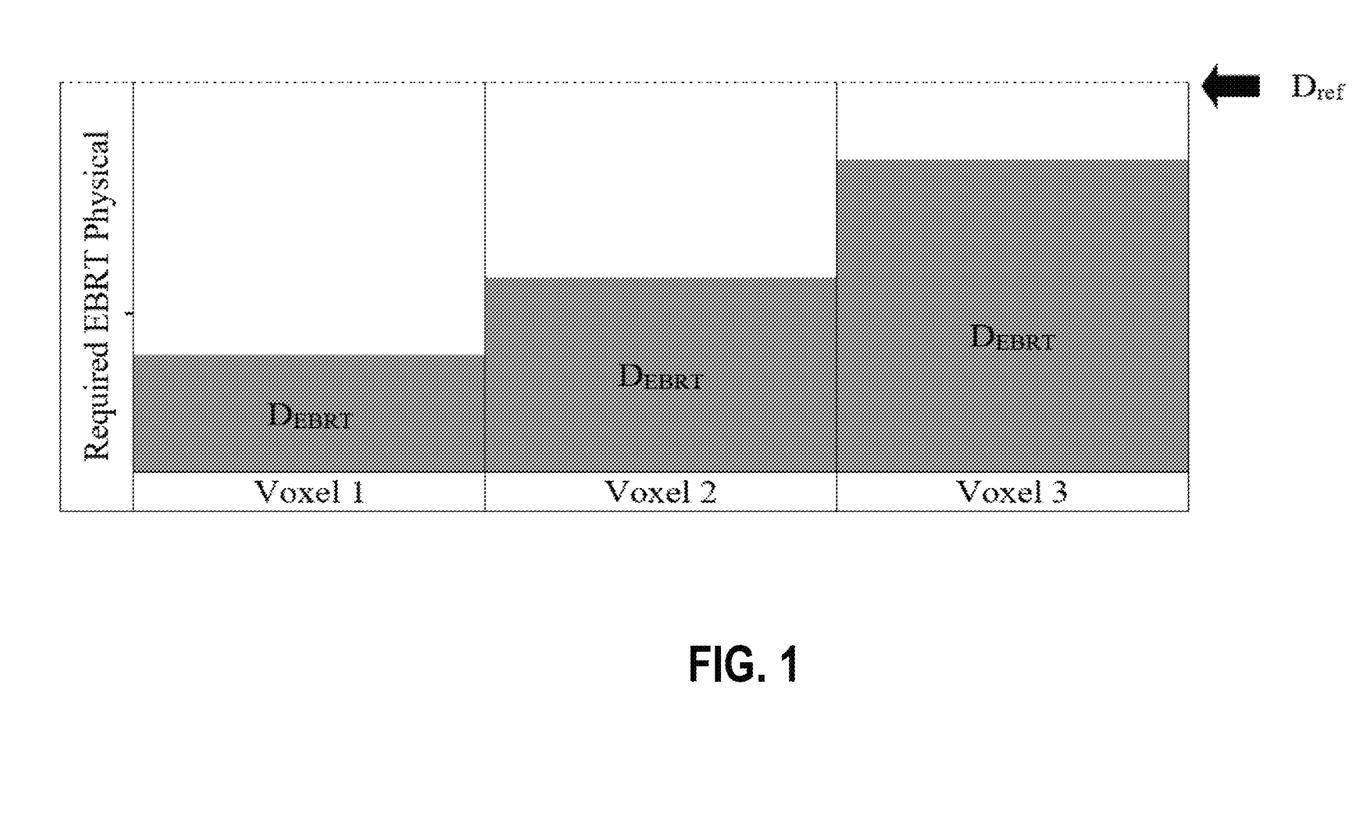
FIG. 1 illustrates desired external beam radiation therapy dose per voxel for an exemplary therapy according to one or more aspects.
Figure 2:
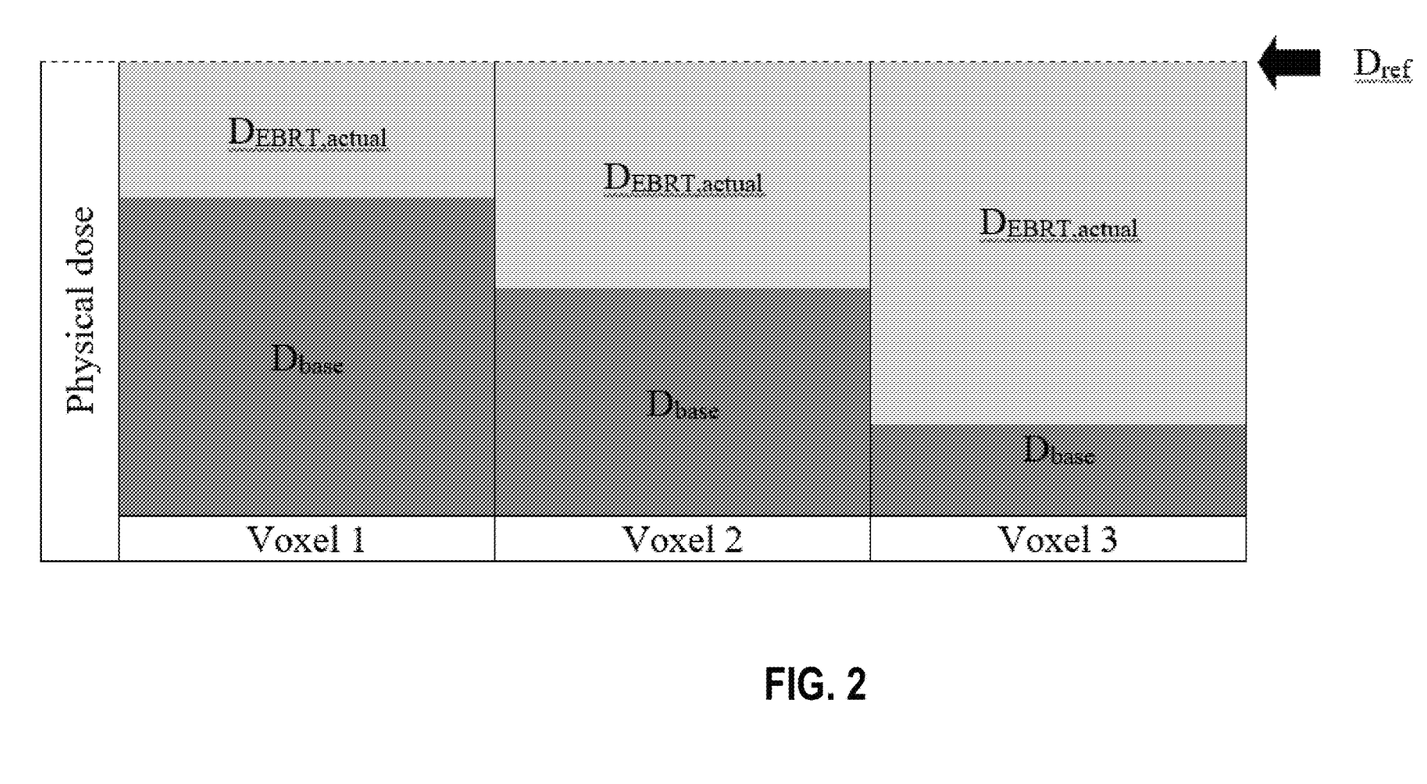
FIG. 2 illustrates a base dose optimization concept to achieve a desired dose distribution in accordance with various aspects.

Performing this calculation on a voxel-by-voxel basis results in a distribution representing the total physical dose from an EBRT plan, consisting of $n_{EBRT}$ fractions, that needs to still needs to be delivered to voxels in the target region and the maximum dose that should be delivered to voxels in organs at risk regions. A schematic representation of this process is shown in FIG. 1. FIG. 1 illustrates the voxel-by-voxel values of $D_{EBRT}$ calculated using Equation 7 for voxels in a target structure. Each dark green box represents the remaining required physical dose for each voxel required from EBRT to result in the desired composite BED.

An additional logistical issue remains to obtain the EBRT dose distribution outlined above. Commercial TPS inverse optimization tools do not allow users to specify the desired physical dose for each voxel, as illustrated in FIG. 1, but instead require the user to specify dose optimization goals that apply to all voxels within a volume of interest (i.e., maximum dose, minimum dose, uniform dose, etc.). To address this issue, a method is proposed that involves calculating a base dose ($D_{base}$) for each voxel. $D_{base}$ is equal to the difference between the physical dose corresponding to the $BED_{ref}$ calculated for the number of fractions for the future EBRT treatment ($D_{ref}$) and the $D_{EBRT}$.

$$D_{base} = D_{ref} - D_{EBRT} \qquad \text{Equation 8}$$

$D_{ref}$ is a structure-specific value for each target or OAR volume and is defined as the total physical dose that, when delivered in $n_{EBRT}$ fractions, results in the $BED_{ref}$. For target structures this represents the desired minimum physical dose value with a BED corresponding to those of the reference prescription tumor dose and for OARs this is the maximum physical dose value with a BED corresponding to that of commonly used maximum dose constraints from conventional RT. An expression for $D_{ref}$ is derived similarly to Equation 6, except the BED term is given by $BED_{ref}$:

$$D_{ref} = \frac{n_{EBRT}(\alpha/\beta)}{2}\left(-1 + \sqrt{1 + \frac{4BED_{ref}}{n_{EBRT}(\alpha/\beta)}}\right) \qquad \text{Equation 9}$$

Substitution of Equations 6 and 9 into Equation 8 and simplifying terms results in an expression for $D_{base}$:

$$D_{base} = \frac{n_{EBRT}(\alpha/\beta)}{2}\left(\sqrt{1 + \frac{4BED_{ref}}{n_{EBRT}(\alpha/\beta)}} - \sqrt{1 + \frac{4(BED_{ref} - BED_{prior})}{n_{EBRT}(\alpha/\beta)}}\right) \qquad \text{Equation 10}$$

Performing this calculation on a voxel-by-voxel basis results in a base dose distribution that is intended to be imported into an EBRT TPS. In some exemplary implementations herein, inverse optimization will be employed to generate EBRT plans. Modern TPS platforms offer the ability to specify a "base dose" or "bias dose" to allow an EBRT plan to be generated so that the sum of the base dose and new EBRT plan attempt to achieve the input optimization goals. This technique will be used to account for dose delivered by the prior treatment by optimizing an EBRT plan so that the sum of the dose to each voxel from the IMRT plan ($D_{EBRT,actual}$) and $D_{base}$ is equal to $D_{ref}$ for voxels in a target volume and less than $D_{ref}$ for all non-target voxels.

In an embodiment where a TPS supports voxel-wise rather than contour-wise dose objectives, or currently if a contour is defined for every voxel, $D_{EBRT}$ could be also imported directly into the TPS to define the voxel-wise desired dose component from the EBRT course or the optimizer could compute Equation 8 within its objective function to incorporate the already delivered $D_{base}$ when optimizing $D_{EBRT}$ to achieve $D_{ref}$.

Exemplary Planning Procedure

An exemplary planning procedure based on the concepts above may commence with acquiring previous treatment planning CT and/or MRIs with corresponding target and organ at risk (OAR) structures and previously delivered dose distributions ($D_{prior}$) following base radiotherapy (RT) treatment and importing into a TPS program.

A secondary EBRT radiotherapy simulation CT is performed and imported into the TPS program.

Figure 3:
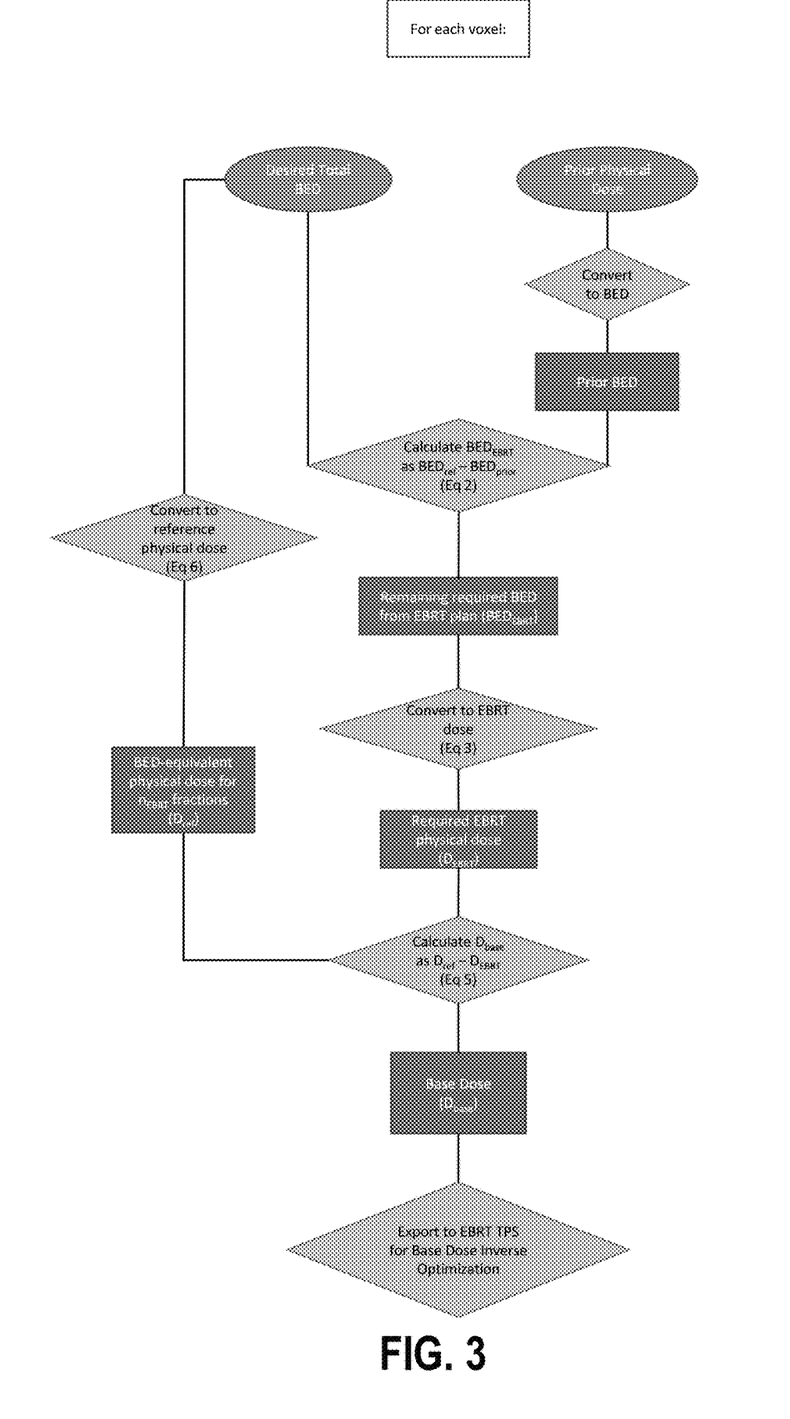
FIG. 3 is a schematic block diagram of an exemplary, non-limiting embodiment for base dose determination according to one or more aspects.

Subsequently, tools provided in the TPS may be utilized to register the previous imaging and second radiotherapy simulation imaging. In cases where acceptable anatomic fusion is not possible due to tissue/cavity deformation, deformable image registration may be used. Dose from the previous treatment is mapped onto the secondary EBRT simulation CT using the image registration. If deformable registration tools are used, the $D_{prior}$ distribution may be deformably mapped using the deformation registration information. Then, secondary RT planning contours are generated. Next, $BED_{ref}$ and pertinent tissue-specific BED parameters (i.e., etc.) for each RT planning contour are specified. The tissue-specific BED parameters are used to convert the prior treatment physical dose mapped onto the EBRT simulation CT to $BED_{prior}$ using the appropriate BED model. Finally, $D_{base}$ is calculated using Equation 10 for each voxel on the EBRT simulation CT. FIG. 3 illustrates the conversion process.

The secondary EBRT simulation CT, secondary RT planning contours, and $D_{base}$ distribution are then imported into a secondary EBRT treatment planning system. For this step, the pertinent DICOM header information (e.g. patient demographic values) in the base TPS may be edited to ensure the information matches the data in the secondary TPS to avoid import incompatibility issues. An RT plan ($D_{EBRT,actual}$) is generated using inverse optimization tools with the base dose as a foundation to achieve the dose objectives. The composite dose distribution consisting of the sum of $D_{base}$ and $D_{EBRT,actual}$ is evaluated and re-optimized, if needed, until an acceptable secondary RT plan is generated.

In other embodiments, the conversion from base RT physical dose to $D_{base}$ may be computed using a separate third dose conversion system. And in other embodiments the conversion from base RT physical dose to $D_{base}$ may be computed using the secondary RT TPS.

Improved Determination of Base Dose

In the clinic, if a patient is getting external beam radiotherapy following any prior radiotherapy (e.g. radioembolization, molecular radiotherapy, brachytherapy, proton therapy, etc.) or other techniques that may affect the surviving fraction of cells, the expected biological implications must be accounted for in order to define a prescription dose which will optimize treatment outcomes. One conventional approach to this is either (I) non-voxelized estimation using models on summarized values from the dose distribution or (II) biological treatment planning plugins, which are expensive, not widely adopted, and do not conceive of building one treatment onto another where the treatments have different biologic dose effects.

Described herein is a general and improved technique for determining a base dose employed in treatment planning. Using this technique, prior therapy doses are considered on a voxelized basis such that subsequent treatments may be planned. The base dose output is operable with legacy treatment planning systems and is not computationally intensive.

As noted above, a biologically effective dose (BED) is a more useful quantity to express expected biological effects of radiation therapy or other therapies. Physical dose is not as useful an indicator of biological effects, particularly when considering expected tumor control or normal tissue complication probabilities. When considering situations with multiple treatment sessions and/or treatment utilizing multiple, different therapies, additivity becomes desirable to design a treatment plan that mitigates complications.

In general, a treatment plan may satisfy two conditions. A first condition is a biological condition and provides that a biologically effective dose (BED) of prior treatment(s) in addition to a biologically effective dose (BED) of a planned treatment should achieve a reference or threshold BED. A second condition is a physical condition and provides that a prior physical dose or base dose plus a planned physical dose for a subsequent treatment should achieve a reference dose (e.g. dose constraint). It is to be appreciated that these conditions may be evaluated on a point-by-point basis. In practical terms, since treatment planning is performed based on medical imaging, these conditions may be considered per voxel.

As noted above, conventional treatment planning system (TPS) platforms typically optimize treatment plans based on physical dose. Optimizing based on physical dose (i.e. satisfying the second (physical) condition) may lead to violations of the first (biological) condition using conventional techniques. BED is a non-linear phenomenon. Consideration of physical dose alone does not account for all biological constraints. Similarly, BED is not a direct substitute for physical dose due to its non-linearity.

A technique for determining a base dose is described below. The base dose value determined can be input to conventional TPS platforms that optimize according to physical dose. The base dose is determined such that the TPS platforms, when optimizing for physical dose, consider the biological constraints defined using BED. The base dose does not have a direct physical meaning, but operates as a proxy to enable optimization by the TPS platform to meet a reference BED. The base dose is a value representing, corresponding to, and derived from a BED for prior therapy as opposed to an actual physical dose of the prior therapy.

According to an aspect, the base dose is determined based on a relationship generated between BED and a dose, such as a fractionated dose. According to an embodiment, Equation 4 above can be utilized to define this relationship. For example, the quadratic equation created by distributing, D, can be solved to generate the relationship between D and BED. Further to this embodiment, this value D, defined according to BED, can be used in the model described above. For instance, the expression for D may be utilized in place of the equivalent dose (EQD) and, subsequently, the base dose $D_{base}$ may be determined.

In accordance with various aspects, a base dose determination tool is provided that receives, as input, a biological effective dose (BED) from any therapy and outputs a base dose that may be imported into a treatment planning system to achieve a plan satisfying BED constraints. In some examples, the tool utilizes relationships based on a Linear Quadratic (LQ) BED model as described above.

Figure 4:
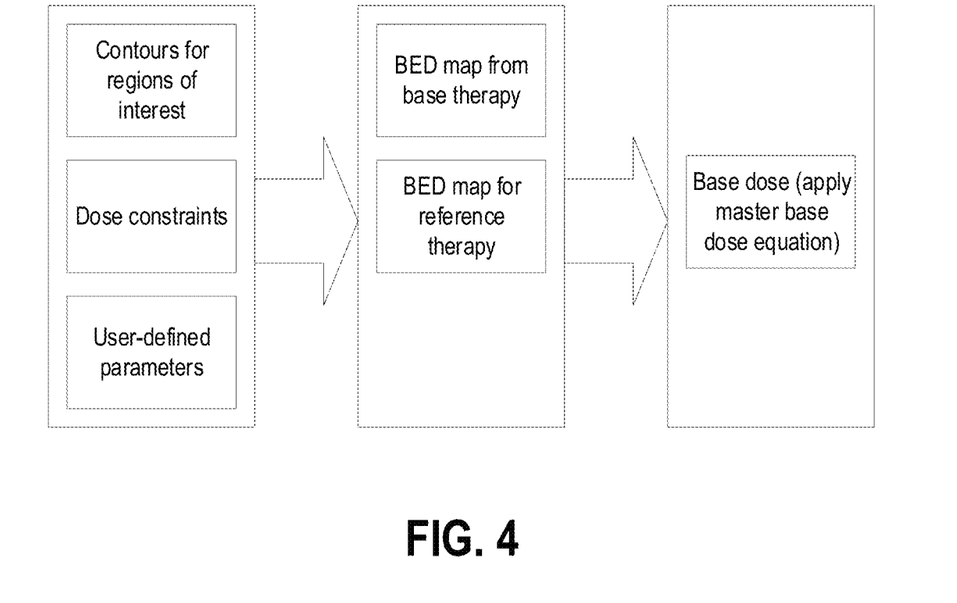
FIG. 4 is a schematic block diagram of an exemplary, non-limiting embodiment for base dose determination according to one or more aspects.

In an embodiment, generally shown in FIG. 4, the tool receives as inputs, for example, contours, user-defined parameters (e.g. radiobiological parameters, etc.), optimization parameters (e.g. dose constraints, and prior therapy BED map registered to a series to be used for treatment planning (e.g. a simulation image). The tool matches contours from the simulation image to ranked tissue-specific user-defined parameters and optimization parameters. The tool may create parameter maps and a reference dose from the ideal plan by substituting the user-defined parameters and optimization parameters into the contours according to rank. Then, the tool may apply the base dose relationship to the parameter maps, reference dose, and prior therapy BED map on a voxel-wise basis. As output, the tool provides a base dose.

In various examples, the contour matching defines how the parameter maps and reference dose are created. The parameter maps and reference dose are required arguments to the base dose relationship, which is utilized to determine the desired voxelized output using a lightweight method.

In an embodiment, the additional therapy may be for a cancer which has a suspected likelihood of recurrence which would subsequently require additional therapy in the future. In this embodiment, the "prior dose" may be a simulated dose anticipated in the future based on a statistical model of location of and time to expected recurrence and required future therapy dosimetry. In this embodiment, the result of the planned therapy optimization is a therapy plan with sufficiently dose-spared OARs to allow safe delivery of future therapy.

Figure 5:
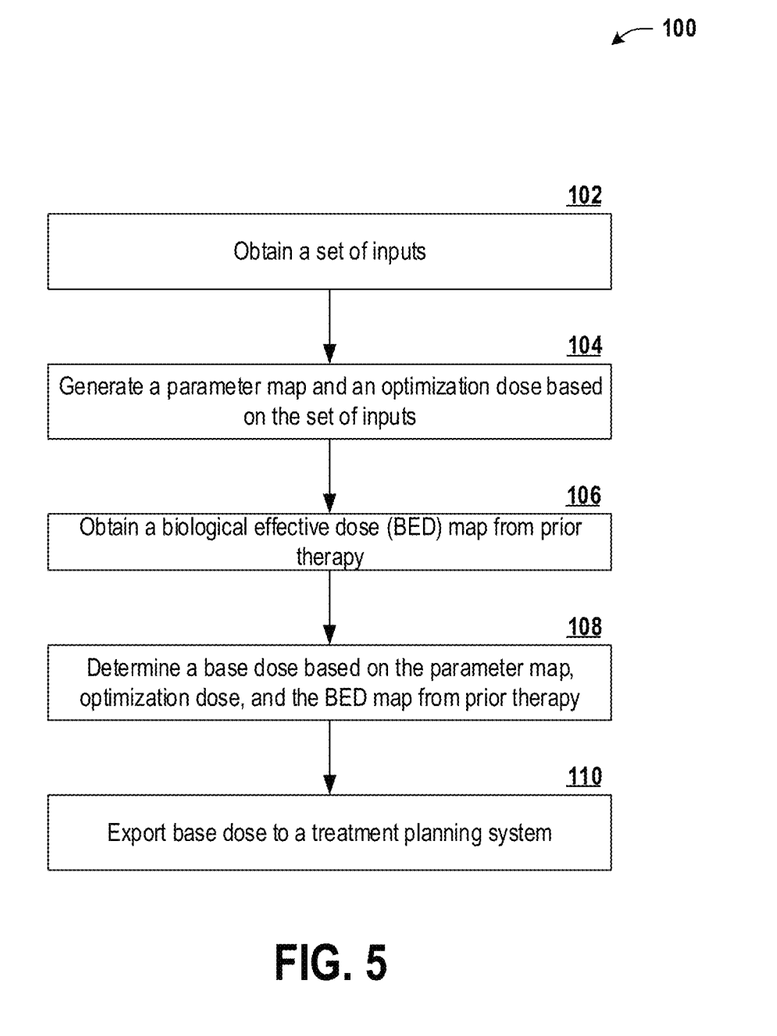
FIG. 5 illustrates an exemplary, non-limiting embodiment of a method for determining a base dose according to various aspects.

FIG. 5 illustrates a flow diagram of an exemplary, non-limiting method 100 for determining a base dose utilized for treatment planning of an additional therapy. In an aspect, method 100 is suitable while planning a radiation therapy that is subsequent to a prior therapy. The additional therapy may or may not be different from the prior therapy. For instance, as in the examples described above, the prior therapy may be LDR BT and the additional therapy may be EBRT. It is to be appreciated, however, that the technique described herein is not limited to these therapies and this technique may be employed for other combinations of therapies including one or more of BT, EBRT, radioembolization, molecular radiotherapy, proton therapy, etc.

Method 100 may begin at 102, where a set of inputs are obtained. The set of inputs may include, for example, contours, radiobiological parameters for the additional therapy, and optimization parameters (e.g. dose constraints). The contours may indicate regions of interest such as, but not limited to, OARs and target volumes. The optimization parameters may be per contour and indicate respective reference doses for the corresponding regions. The radiobiological parameters may also be defined on a per contour basis and may be specific to the therapy. For instance, for EBRT, the biological modeling parameters may include n (e.g. number of fractions) and $\alpha/\beta$ (e.g. indicating tissue-specific radiosensitivities).

At 104, a parameter map and a reference dose is generated based on the set of inputs. The parameter map and reference dose may be generated by matching the contours to the radiobiological parameters and optimization parameters. Once matched, the parameters and optimization parameters may be substituted into the contours to create the maps and reference dose.

At 106, a biological effective dose (BED) map from prior therapy is obtained. As utilized herein, prior therapy may also be referred to as a base therapy. In an aspect, the prior BED map is registered to a simulation image (e.g. a series utilized for treatment planning). The prior BED map provides BED for regions of interest resulting from prior therapy.

At 108, a base dose is determined based on the parameter map, reference dose, and the BED map from prior therapy. For example, the parameter map and reference dose may provide a BED map for additional therapy. Using the relationships described above, the BED map from prior therapy and the parameter map/reference dose are input to the relationship, which produces a base dose suitable for treatment planning. At 110, the base dose is exported to a treatment planning system.

Figure 6:
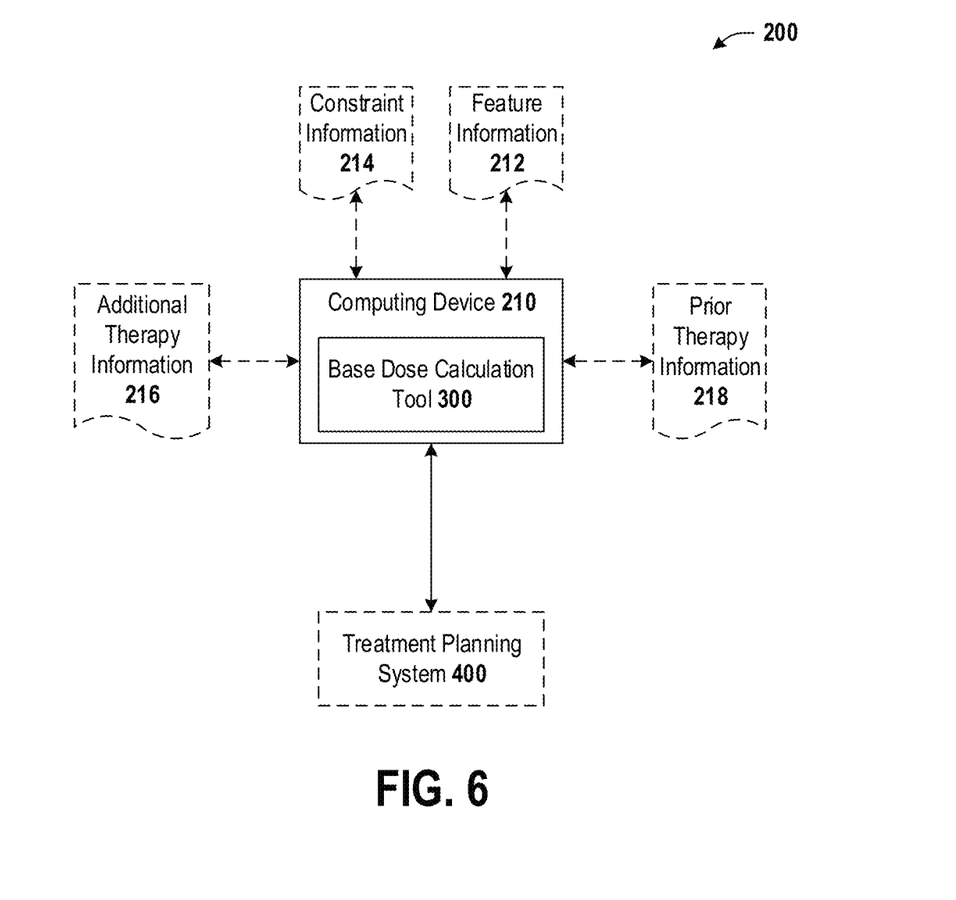
FIG. 6 is a schematic block diagram of an exemplary system for determining a base dose in accordance with one or more aspects.

Turning to FIG. 6, illustrated is a schematic block diagram of an exemplary, non-limiting embodiment for a base dose calculation system 200. As shown, system 200 can include a computing device 210, which implements a base dose calculation tool 300. The computing device 210 can include a processor and various computer-readable storage media (e.g., volatile and non-volatile). The computer-readable storage media can store computer-executable instructions implementing at least a portion of functional modules comprising the base dose calculation tool 300, described herein. When the computer-executable instructions are executed by the processor, the system 200 is thus configured to perform the operations described herein, such as those of method 100 described above.

Computing device 210 can further include various hardware devices (not shown) to implement portions of base dose calculation 300. For instance, computing device 210 can include a graphics device having a graphics processing unit (GPU), dedicated memory, and/or hardware interfaces to couple the graphics device to a display. Moreover, computing device 210 can include physical hardware ports and/or wireless interfaces (e.g., Bluetooth, wireless USB, etc.) to couple computing device 210 to various devices of system 200, such as, but not limited to a treatment planning system 400.

Base dose calculation tool 300, according to an aspect, determines a base dose that is exported to treatment planning system 400 to plan a radiation therapy. Base dose calculation tool 300 acquires feature information 212 indicating various features of interest. For instance, feature information 212 may include contours of regions of interest such as OARs and target volumes. Base dose calculation tool 300 also receives optimization information, such as therapy parameters or dose constraints, 214 that indicates dose constraints for each feature indicated by feature information 212. The base dose calculation tool 300 also obtains additional therapy information 216 and prior therapy information 218. In an aspect, additional therapy information 216 may include radiobiological parameters for a particular additional therapy. The parameters may be provided for each feature indicated by the feature information 212. The prior therapy information 218, in some examples, may be a BED map from prior therapy that is registered to a simulation image. The simulation image may be a DICOM series utilized by treatment planning system 400 during treatment planning. The prior therapy information 218 may also be referred to herein as base therapy information. In addition to information related to a prior or base therapy for a patient, the base therapy information or prior therapy information 218 may include information related to laboratory and/or patient notes. This information may have biological information relevant to biological planning even if no base therapy were performed.

Using these inputs, the base dose calculation tool 300 generates a base dose, which is exported to treatment planning system 400. The base dose may be generated using a base dose relationship derived from the BED model described above.

Figure 7:
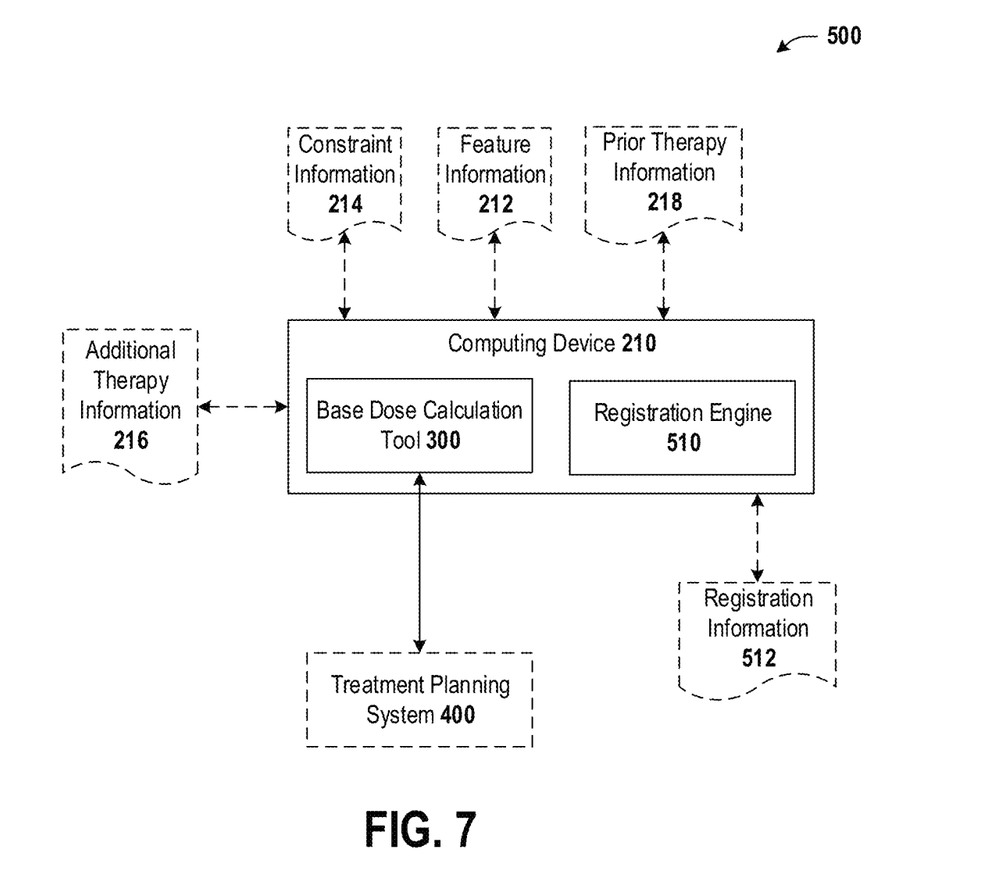
FIG. 7 is a schematic block diagram of an exemplary system for determining a base dose according to various aspects.

Turning to FIG. 7, illustrated is a schematic block diagram of an exemplary, non-limiting embodiment for a base dose calculation system 500. As shown in FIG. 7, system 500 includes the computing device 210, base dose calculation tool 300, and treatment planning system 400. Additionally, in the embodiment of FIG. 7, a registration engine 510 is provided. According to an aspect, the registration engine 510 receives registration information 512 and registers corresponding voxels of various images together. The registration information 512 may, for example, include spatiotemporal registration information that accurately links points in space/time on the various images together. The registration engine 510, in an aspect, provides a consistent basis for the base dose calculation tool 300 to determine and manipulate BED quantities when determining the base dose value.

Figure 8:
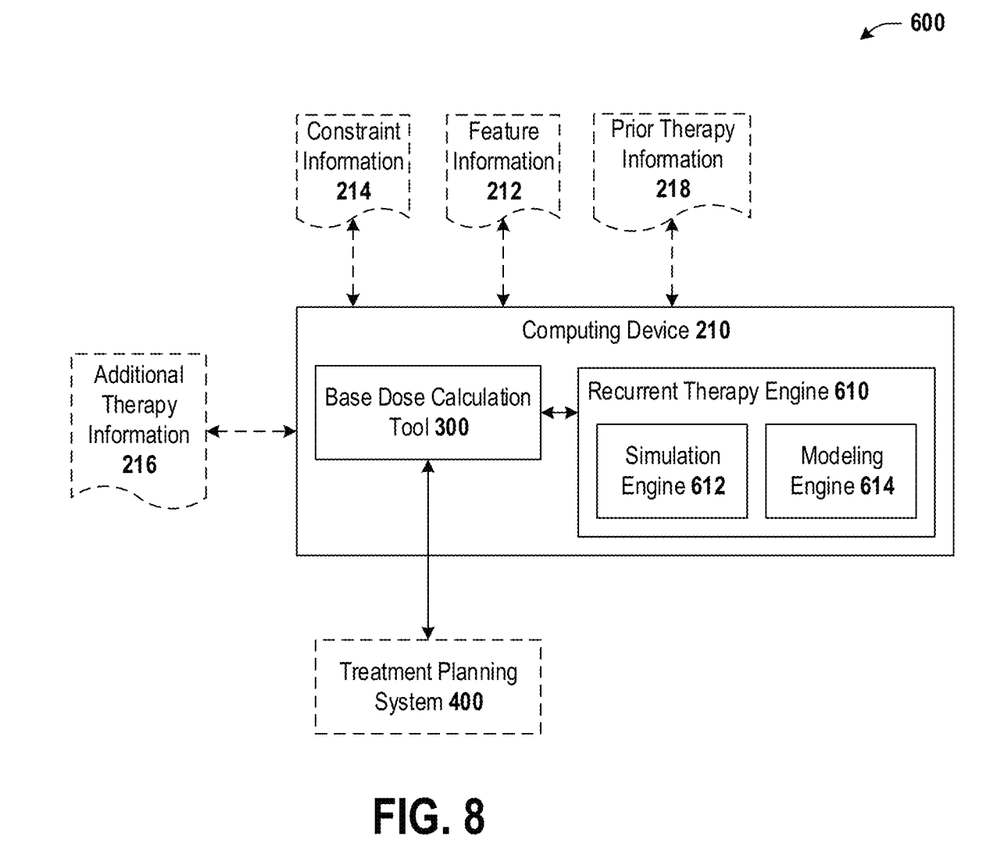
FIG. 8 is a schematic block diagram of an exemplary system for determining a base dose in accordance with one or more aspects.

Turning to FIG. 8, illustrated is a schematic block diagram of another exemplary, non-limiting embodiment for a base dose calculation system 600. As shown in FIG. 7, system 600 includes the computing device 210, base dose calculation tool 300, and treatment planning system 400. Additionally, in the embodiment of FIG. 8, a recurrent therapy engine 610 is provided. As mentioned above, the additional therapy may be for a cancer, which has a suspected likelihood of recurrence. Recurrence may subsequently require additional therapy in the future. In this embodiment, base therapy information 218 may include information related to location of and time to expected recurrence, which is received by a modeling engine 614 to generate a predictive model or time and location of recurrence. The simulation engine 612 may use the predictive model to generate a simulated therapy to be delivered in the future, and based on the simulated therapy, a predicted or future therapy dosimetry. This prediction may be utilized by the base dose calculation tool 300 to determine base dose value exported to the treatment planning system 400 for future planning of this recurrent therapy.

Figure 9:
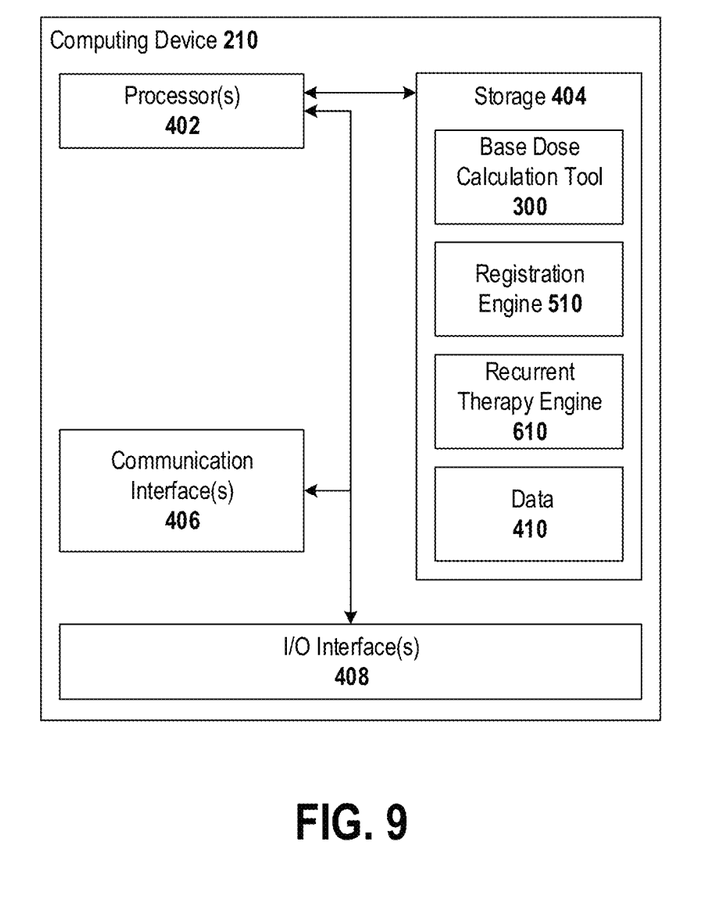
FIG. 9 is a schematic block diagram of an exemplary, non-limiting embodiment for a computing device associated with the system of FIGS. 6-8.

FIG. 9 illustrates a schematic block diagram of an exemplary, non-limiting embodiment for a computing device 210 associated with system 200 of FIG. 7. As shown in FIG. 8, computing device 210 includes one or more processor(s) 402 configured to execute computer-executable instructions such as instructions composing base dose calculation tool 300, registration engine 510, and recurrent therapy engine 610. Such computer-executable instructions can be stored on one or more computer-readable media including non-transitory, computer-readable storage media such as storage 404. For instance, storage 404 can include non-volatile storage to persistently store base dose calculation tool 300, registration engine 510, recurrent therapy engine 610, and/or data 410 (e.g., parameters, contours, BED maps, feature information, working data, etc.). Storage 404 can also include volatile storage that stores base dose calculation tool 300, registration engine 510, recurrent therapy engine 610, and other data 410 (or portions thereof) during execution by processor 402.

Computing device 210 includes a communication interface 406 to couple computing device 210 to various remote systems (e.g. treatment planning system, etc.). Communication interface 406 can be a wired or wireless interface including, but not limited to, a WiFi interface, an Ethernet interface, a fiber optic interface, a cellular radio interface, a satellite interface, etc. An I/O interface 408 is also provided to couple computing device 210 to various input and output devices such as displays, touch screens, keyboards, mice, touchpads, etc. By way of example, I/O interface 408 can include wired or wireless interfaces such as, but not limited to, a USB interface, a serial interface, a WiFi interface, a short-range RF interface (Bluetooth), an infrared interface, a near-field communication (NFC) interface, etc.

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

In addition, while a particular feature of the disclosure may have been disclosed with respect to only one of several implementations, such features may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof

What is claimed is:

1. A system, comprising:
a processor coupled to memory storing computer-executable instructions that, when executed by the processor, configure the processor to:
obtain base therapy information for a patient;
obtain additional therapy information related to an additional therapy to be performed on the patient;
determine a base dose distribution based on the base therapy information and the additional therapy information, and in accordance with a base dose relationship derived from a biological effective dose (BED) model associated with the additional therapy; and
export the base dose distribution to a treatment planning system for planning the additional therapy.

2. The system of claim 1, wherein the base therapy is a different therapy than the additional therapy.

3. The system of claim 1, wherein the base therapy is a simulated therapy to be delivered in the future.

4. The system of claim 3, wherein the base therapy information includes a predictive model of time and location of recurrence.

5. The system of claim 1, wherein the base therapy information includes a BED map from the base therapy registered to a simulation image.

6. The system of claim 1, wherein the additional therapy information includes at least feature information indicating features of interest, optimization information indicating at least dose optimization parameters for each feature indicated by the feature information, and user-defined parameters associated with the additional therapy for each feature indicated by the feature information.

7. The system of claim 6, wherein the processor is further configured to:
match the features in the feature information to respective user-defined parameters and optimization parameters;
substitute the user-defined parameters and optimization parameters, as mapped, to generate a BED map for the additional therapy.

8. The system of claim 7, wherein the processor is further configured to determine the base dose distribution based on the BED map for the additional therapy and the base therapy information.

9. The system of claim 1, wherein the base dose relationship converts a BED to a physical dose distribution suitable for the treatment planning system.

10. A method, comprising:
obtaining base therapy information for a patient;
obtaining additional therapy information related to an additional therapy to be performed on the patient;
determining a base dose distribution based on the base therapy information and the additional therapy information, and in accordance with a base dose relationship derived from a biological effective dose (BED) model associated with the additional therapy; and
exporting the base dose distribution to a treatment planning system for planning the additional therapy.

11. The method of claim 10, wherein the base therapy is a different therapy than the additional therapy.

12. The method of claim 10, wherein the base therapy is a simulated therapy to be delivered in the future.

13. The method of claim 12, wherein the base therapy information includes a predictive model of time and location of recurrence.

14. The method of claim 10, wherein the base therapy information includes a BED map from the base therapy registered to a simulation image.

15. The method of claim 10, wherein the additional therapy information includes at least feature information indicating features of interest, optimization information indicating at least constraints for each feature indicated by the feature information, and user-defined parameters associated with the additional therapy for each feature indicated by the feature information.

16. The method of claim 15, further comprising:
matching the features in the feature information to respective user-defined parameters and constraints;
substituting the user-defined parameters and constraints, as mapped, to generate a BED map for the additional therapy.

17. The method of claim 16, further comprising determining the base dose distribution based on the BED map for the additional therapy and the base therapy information.

18. The method of claim 10, wherein the base dose relationship converts a BED to a physical dose distribution suitable for the treatment planning system.

19. A non-transitory, computer-readable storage medium having stored thereon computer-executable instructions for a base dose calculation tool, the instructions, when executed, configure a processor to:
obtain base therapy information related to a base therapy for a patient;
obtain additional therapy information related to an additional therapy to be performed on the patient;
determine a base dose distribution based on the base therapy information and the additional therapy information, and in accordance with a base dose relationship derived from a biological effective dose (BED) model associated with the additional therapy; and
export the base dose distribution to a treatment planning system for planning the additional therapy.

20. The non-transitory, computer-readable storage medium of claim 19, wherein the base therapy is a different therapy than the additional therapy.

21. The non-transitory, computer-readable storage medium of claim 19, wherein the base therapy is a simulated therapy to be delivered in the future.

22. The non-transitory, computer-readable storage medium of claim 21, wherein the base therapy information includes a predictive model of time and location of recurrence.

23. The non-transitory, computer-readable storage medium of claim 19, wherein the base information includes a BED map from the base therapy registered to a simulation image.

24. The non-transitory, computer-readable storage medium of claim 19, wherein the additional therapy information includes at least feature information indicating features of interest, optimization information indicating optimization parameters for each feature indicated by the feature information, and user-defined parameters associated with the additional therapy for each feature indicated by the feature information.

25. The non-transitory, computer-readable storage medium of claim 24, wherein the processor is further configured to:
match the features in the feature information to respective user-define parameters and optimization parameters;
substitute the user-define parameters and optimization parameters, as mapped, to generate a BED map for the additional therapy; and determine the base dose distribution based on the BED map for the additional therapy and the base information.

26. The non-transitory, computer-readable storage medium of claim 25, wherein the base dose relationship converts a BED to a physical distribution suitable for the treatment planning system.

* * * * *